US012697067B2

(12) United States Patent
Zhu et al.

(10) Patent No.: US 12,697,067 B2
(45) Date of Patent: Aug. 4, 2026

(54) HEARING AID WITH EAR EEG RECORDING

(71) Applicant: Oticon A/S, Smørum (DK)

(72) Inventors: Lin Zhu, Smørum (DK); Gunnar Gudnason, Smørum (DK); Seri Jalonen, Smørum (DK); Xiaodong Liu, Smørum (DK); Peter Søren Kirk Hansen, Smørum (DK)

(73) Assignee: OTICON A/S, Smørum (DK)

( * ) Notice: Subject to any disclaimer, the term of this patent is extended or adjusted under 35 U.S.C. 154(b) by 1156 days.

(21) Appl. No.: 17/697,238

(22) Filed: Mar. 17, 2022

(65) Prior Publication Data

US 2022/0296166 A1     Sep. 22, 2022

(30) Foreign Application Priority Data

Mar. 18, 2021     (EP) ..................................... 21163402

(51) Int. Cl.
*A61B 5/256* (2021.01)
*A61B 5/00* (2006.01)
*H04R 25/02* (2006.01)

(52) U.S. Cl.
CPC ............ *A61B 5/6815* (2013.01); *A61B 5/256* (2021.01); *H04R 25/02* (2013.01); *H04R 2225/021* (2013.01)

(58) Field of Classification Search
CPC ......... A61B 5/256; A61B 5/291; A61B 5/305; A61B 5/30; A61B 5/31; A61B 5/6815;
(Continued)

(56) References Cited

U.S. PATENT DOCUMENTS

2002/0063592 A1*   5/2002   McKim, Jr. ............ G01R 19/14
                                                               327/307
2010/0317955 A1   12/2010   Madsen et al.
(Continued)

OTHER PUBLICATIONS

Guermandi, Marco, et al. "Active electrode IC for EEG and electrical impedance tomography with continuous monitoring of contact impedance." IEEE transactions on biomedical circuits and systems 9.1 (2014): 21-33. (Year: 2015).*
(Continued)

*Primary Examiner* — Eric J Messersmith
(74) *Attorney, Agent, or Firm* — Birch, Stewart, Kolasch & Birch, LLP

(57)     ABSTRACT

A hearing aid includes a plurality of electrode units, where each of the plurality of electrode units includes an electrode configured to provide an electrical stimulation to a user of the hearing aid and/or to measure a bio response signal of the user; a plurality of electrode channel circuits, where each of the plurality of electrode channel circuits includes: an operational amplifier comprising a first input terminal configured to receive the bio response signal and provide an amplified bio response signal, and the operational amplifier includes a first load input; a first DC offset unit configured to reduce the impact of DC offset in the electrode channel circuit of the plurality of electrode channel circuits by receiving a part of the amplified bio response signal and converting it to a feedback current signal which is transmitted to the first load input for providing balanced drain currents in the operational amplifier.

18 Claims, 11 Drawing Sheets

(58) Field of Classification Search
CPC ... A61B 5/6817; A61B 5/7203; A61B 5/7225;
A61B 5/369; H04R 2225/021; H04R
25/00; H04R 25/02; H03F 3/45973; H03F
3/45991; A61N 1/36036; A61N 1/36038
See application file for complete search history.

(56) References Cited

U.S. PATENT DOCUMENTS

| | | | |
|---|---|---|---|
| 2013/0131478 A1* | 5/2013 | Simpson ............ | A61B 5/14532 600/347 |
| 2016/0081623 A1 | 3/2016 | Lunner | |
| 2016/0249846 A1* | 9/2016 | Yoo ........................ | G16H 50/20 600/544 |
| 2017/0281037 A1 | 10/2017 | Kidmose et al. | |
| 2020/0306539 A1* | 10/2020 | Kim ..................... | A61N 1/3787 |

OTHER PUBLICATIONS

Yoo, Jerald, et al. "An 8-channel scalable EEG acquisition SoC with patient-specific seizure classification and recording processor." IEEE journal of solid-state circuits 48.1 (2012): 214-228. (Year: 2012).*
Bagheri, Arezu, et al. "Low-frequency noise and offset rejection in DC-coupled neural amplifiers: A review and digitally-assisted design tutorial." IEEE transactions on biomedical circuits and systems 11.1 (2016): 161-176. (Year: 2016).*
Bhargava et al., "A 262nW Analog Front End with a Digitally-Assisted Low Noise Amplifier for Batteryless EEG Acquisition", SOI-3D-Subthreshold Microelectronics Technology Unified Conference, IEEE, XP032731301, Oct. 6, 2017, pp. 1-2.
Extended European Search Report issued in 21163402.7, dated Sep. 13, 2021.

* cited by examiner

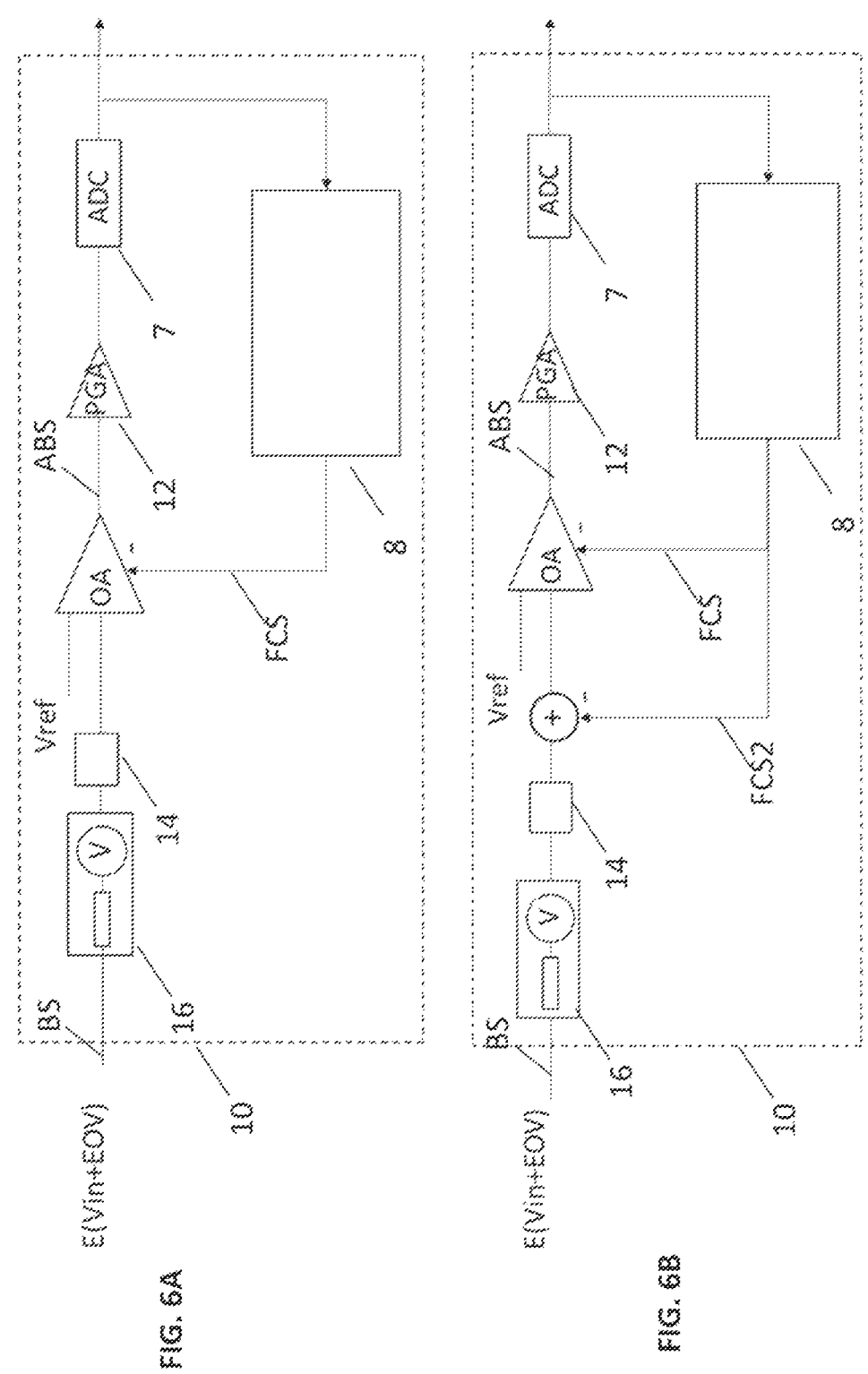

HEARING AID WITH EAR EEG RECORDING

FIELD

The present disclosure relates to a hearing aid with electrode units for recording bio response signals, e.g. Electroencephalography (EEG) signal, of a user of the hearing aid, and the hearing aid includes an improved EEG topology.

BACKGROUND

Bio response signals are here understood to be electrical potential differences originating from a living body. Well-known examples are Electrocardiogram (ECG) signals and Electroencephalogram (EEG) signals. An ear component for detecting bio response signals at the ear is often made for the detection of EEG signals, but could also be applied for detecting other bioelectrical signals such as ECG, electrooculography (EOG), or muscular activity.

EEG signals are electrical signals generated by a person's brain activity. In recent years, EEG monitoring systems, that may be carried or worn continuously by a person to be monitored, have been devised. A goal is to have personal wearable EEG monitors, which can be carried without causing more inconvenience than glasses or a modern small hearing aid.

Such EEG monitors may be applied for different purposes. One example is surveillance of a condition of a person and e.g. for providing an alarm or information in case predetermined conditions are met. The monitor may also be applied for collection of data, e.g. for diagnostic purposes or for research use. Examples of applications are for surveillance of persons having diabetes or epilepsy. Another example is as input to the control or adjustment of a hearing aid.

Furthermore, electric potentials originating from neural activity in the cranial nerves and in the brain stem may also be measured with hearing aids. This is e.g. relevant in assessment of hearing loss, where it is common to measure responses from the cranial nerve (cranial nerve 8) and from the brain stem (as in auditory brain stem responses). But it may also be relevant to measure responses from or stimulation of e.g. the vagus nerve (cranial nerve 10) which have branches out in the external ear. This may e.g. be of relevance in epilepsies.

Electrophysiological signals, i.e. bio response signals, are normally weak in amplitude compared with surrounding interferences. For example, bio response signals such as electroencephalography (EEG) signals are in the range of 10 μv-100 μv measured by non-invasive electrodes, and electrocardiogram (ECG) signals are in the range of 100 μv to 1 mV measured by non-invasive electrodes, and coupling interferences from surrounding could easily be in millivolt-level or even volt-level. Most of these interferences normally appear in common mode along with the bio response signals. Therefore, the interference immunity is of significant importance for bio response signal recording. In traditional solutions to provide an improved interference immunity, an electrode offset voltage (EOV) is compensated at an input of an amplifier. A digital-analog converter (DAC) is normally connected to the input of the amplifier which would impose fairly strict requirements to the reference of the DAC, especially in terms of Power Supply Rejection Ratio (PSRR) and/or Common Mode Rejection Ration (CMRR). In addition, the DAC always introduces transient spikes, that would appear at the input of the amplifier and result in harmonic distortion at the output of the operational amplifier. The amplifier may be chopping amplifier configured to reduce flicker noise of an operational amplifier.

CMRR of an operational amplifier is the rejection of unwanted input signals common to both input terminals, relative to the wanted difference signal.

PSRR of an operational amplifier is the ratio of the change in supply voltage to the equivalent (differential) output voltage it produces.

Furthermore, electrodes used for recording bio response signals and/or stimulating varies significantly on half-cell potential and resistance. For example, the half-cell potential varies between −300 mV to +300 mV minimum, and the resistance varies from 20 k to 10M even above. Therefore, it is very challenging to reach a good CMRR and/or PSRR under these conditions.

It is of importance to improve noise or interference immunity in the recording of the bio response signal, and to improve the recording's tolerability to variations in electrodes.

SUMMARY

An aspect of the disclosure is to provide a hearing aid with improved bio response recording performance by minimizing DC offset voltage and providing an enhancement in PSRR, and a reduction in CMRR.

According to a first aspect, a hearing aid comprising a plurality of electrode units, where each of the plurality of electrode units includes an electrode configured to provide an electrical stimulation to a user of the hearing aid and/or to measure a bio response signal of the user.

An electrode unit of the plurality of electrode units may include an active electrode that is used for bio response recordings, especially for advanced electrode technology like non-contact and dry-contact electrode. The purposes of employing active electrode are shielding the electrode from external interferences and compensating parasitic capacitances. Compared to a passive electrode, the active electrode generally provides better immunity against surrounding interferences, capacitive coupled interferences as for example Power Line Interference (PLI). Therefore, they are suitable for emerging applications in wearable bio response recording. The active electrode may be combined with right-leg-driven technique. In general, an active electrode holds several advantages including sufficient low input-referred noise, high input impedance and low bias current, low input referred offset, low output impedance, high Common Mode Rejection Ratio (CMRR) and Power Supply Rejection Ratio (PSRR), and for hearing aid devices a low power consumption.

Furthermore, the hearing aid may comprise a plurality of electrode channel circuits, where each of the plurality of electrode channel circuits includes an operational amplifier comprising a first input terminal configured to receive the bio response signal and provide an amplified bio response signal; a first DC offset unit configured to reduce the DC offset in the electrode channel circuit of the plurality of electrode channel circuits by receiving a part of the amplified bio response signal and converting it to a feedback current signal which may be transmitted to a first load input or the first input terminal of the operational amplifier for providing balanced drain currents in the operational amplifier.

Each of the plurality of electrode channel circuits may be differential, which means that two electrode units (part of the plurality of electrode units) are connected to a single electrode channel circuit of the plurality of electrode channel circuits. One of the two electrode units may be a common electrode for at least two of the plurality of electrode channel circuits, and the common electrode unit may be used as a reference electrode in the two electrode channel circuits.

Each of the plurality of electrode units may be connected to an electrode channel circuit of the plurality of electrode channel circuits for improving the quality of the bio response signal or for applying a stimulation to the user via the electrode unit.

The operational amplifier may be a differential amplifier where the first input terminal is a differential input terminal.

The operational amplifier may have a second load input configured to receive a reference voltage. The second load input may be a positive power supply port and the first load input may be a negative power supply port.

The first input terminal of the operational amplifier may be an inverted or non-inverted port.

The operational amplifier includes drain currents including a first drain current and a second drain current, and when the first and second drain currents are equal or about equal then the operational amplifier includes balanced drain currents.

The input to the first DC offset unit may be connected to the output of the operational amplifier and the output of the first DC offset unit may be connected to the first load input. The first DC offset unit may be configured to reduce the DC offset that may be applied to the amplified bio response signal. The reduced DC offset voltage results in that the PSRR requirements for a reference voltage to the operational amplifier is largely relieved. Furthermore, transient spikes in the amplified bio response signal are also removed because of the isolated connection of the output of the first DC offset unit to the first load input.

Each of the plurality of electrode channel circuits may include a second DC offset unit configured to receive the bio response signal and reduce the DC offset and forward the bio response signal with reduced DC offset to the operational amplifier. The input of the second DC offset unit may be connected to an electrode unit of the plurality of electrode units, and the input may be configured to receive the bio response signal recorded by the electrode unit. The second DC offset unit may be connected to the first input terminal of the operational amplifier. The second DC offset unit is configured to partly remove the DC offset voltage at the input of the operational amplifier, and thereby, enhancing PSRR. Having also the first DC offset unit in combination provides an even more improved reduction of the DC offset voltage with minimal cost of signal strength of the bio response signal.

The hearing aid may comprises an analog-to-digital converter, wherein the amplified bio response signal may be converted to a digital electrical signal via the analog-to-digital converter, and the first DC offset unit may include an offset correction circuit configured to receive the digital electrical signal and provide a digital offset correction signal based on a measure of a DC offset voltage in the digital electrical signal. The first DC offset unit includes a first digital-to-analog converter configured to receive the digital offset correction signal and convert it to the feedback current signal which may then be transmitted to the first load input of the operational amplifier.

The first DC offset unit may include a second digital-to-analog converter configured to receive the digital offset correction signal and convert it to another feedback current signal which may then be transmitted to a second input of the operational amplifier or the first input terminal of the operational amplifier combined with the bio response signal.

By combining the first digital-to-analog converter and the second digital-to-analog converter for providing the feedback current signal to the first load input and to the first input terminal of the operational amplifier, respectively, provides an advantage in view of having only one feedback current signal. The PSRR requirement for a reference voltage to the operational amplifier and the transient spikes are largely relieved, since only a portion of DC offset voltage is compensated at the input of the operational amplifier. The CMRR performance is improved as well.

In another example, the first DC offset unit may include a controller configured to provide a control signal based on the digital-electrical signal, an offset storage capacitor connected to the first input terminal of the operational amplifier or the first load input, a pulse current source configured to increase or decrease in discrete steps a voltage level of the offset storage capacitor based on the control signal, and wherein the offset storage capacitor is configured to maintain the voltage level at a level proportional to a DC offset voltage at the first input terminal or at the first load input for providing the balanced drain currents of the operational amplifier.

By replacing the DAC with the offset storage capacitor avoids the problem of noise added by a digital-to-analog converter (DAC) and the power consumption of the DAC.

The controller may be configured to determine the discrete steps by changing a magnitude and/or a duration of the current pulses provided by the pulse current source, and thereby, the duty cycle of the pulse current source can be controlled such that a very small duty cycle can be obtained for limiting the power consumption of the pulse current source to a minimum. Normally, a DAC is driven with a 100% duty cycle, and that results in a power consumption that is significantly higher in comparison to when using the pulse current source.

In yet another example, the first DC offset unit may include the first digital-to-analog converter, the offset storage capacitor the controller and the pulse current source, and thereby the second digital-to-analog converter is avoided, and similar advantages are obtained as if both the first and the second digital-to-analog converter were used. Thus, additional advantages are obtained, for example the additional noise provided by the second digital-to-analog converter is avoided and the power consumption of the second digital-to-analog converter is avoided.

The pulsed current source may be turned on and off based on an input from the controller, where a DC offset is detected or a DC offset that is above a DC offset threshold is detected by the controller, the pulsed current source is turned on, and where a DC offset is not detected or a DC offset that is below a DC offset threshold is detected by the controller, the pulsed current source is turned off. Thereby, the pulsed current source is only in use when needed, and when combining this with a small duty cycle, the power consumption of the pulsed current source is reduced even more in comparison to only have a small duty cycle.

The second DC offset unit may include a shunt impedance circuit including multiple shunt resistors and a voltmeter configured to measure an output voltage of an output of the second DC offset unit, and wherein the impedance matching unit may be configured to match the first impedance to the at least second impedance based on a first measured output voltage of a primary second DC offset unit connected to the first electrode unit and on a second measured output voltage of a secondary second DC offset unit connected to the second electrode unit.

The operational amplifier may be biased at different DC operating point if the DC offset voltage (or electrode offset voltage) becomes large leading to a bad CMRR. However, this is remedied by applying an impedance matching unit to each of the plurality of electrode channel circuits.

Each of the plurality of electrode channel circuits may include an impedance matching unit configured to receive the bio response signal and to match a first impedance of a first electrode unit of the plurality of electrode units to at least a second impedance of a second electrode unit of the plurality of electrode units. An input of the impedance matching unit may be connected to an electrode unit of the plurality of electrode units configured to receive the bio response signal, and an output of the impedance matching unit may be connected to the first input terminal of the operational amplifier or the input of the second DC offset unit.

The impedance matching unit may be configured to receive the bio response signal and forward the impedance matched bio response signal to the operational amplifier or to the second DC offset unit.

By combining the use of the impedance matching unit and the first DC offset unit will result in an improved recording performance as both CMRR is improved while the offset voltage is also reduced or minimized.

The hearing aid may comprise a stimulator unit may be configured to apply an alternating current, a direct current or a combination of an alternating current to at least an electrode unit of the plurality of electrode units, and where the at least electrode unit may be configured to apply the electrical stimulation based on the current.

By applying the alternating current via a first electrode unit of the plurality of electrode units and recording one or more bio response signals via a second electrode unit of the plurality of electrode units, it is possible to determine both a resistive impedance and a reactive impedance, such as a capacitance impedance and/or an inductive impedance. By being possible to determine both impedances provides a more reliable way of determine the impedance, and thereby, an improved CMRR performance is obtained.

The stimulator unit may be configured to transmit the alternating current, the direct current or the combination of the alternating current and the direct current to a first impedance matching unit of a first electrode channel circuit of the plurality of electrode channel circuits, wherein the first impedance matching unit may be configured to forward the current to a first electrode unit of the plurality of electrode units.

A second impedance matching unit of a second electrode channel circuit of the plurality of electrode channel circuits may be configured to measure a plurality of impedances of a second electrode unit of the plurality of electrode units, and based on the plurality of measured impedances both a resistive impedance and/or a reactive impedance of a second electrode unit of the plurality of electrode units are determined.

The hearing aid may be configured to compensate a hearing loss of a user of the hearing aid, comprising a microphone configured to receive an acoustic wave and provide an audio signal based on the acoustic wave, a signal processor unit configured to process the audio signal and provide a processed audio signal, an output transducer configured to output the processed audio signal to the user, and wherein the signal processor unit may be configured to process the audio signal based on the amplified bio response signal or may be configured to adapt a hearing profile stored within a memory of the hearing aid based on the amplified bio response signal.

The hearing aid may comprise an in-the-ear unit; a behind-the-ear unit; a communication link configured to provide an electrical connection between the in-the-ear unit and the behind-the-ear unit, a processor unit configured to receive the amplified bio response signal via the communication link, and wherein one or more of the plurality of electrode units are arranged in the in-the-ear unit, and the processor unit is arranged in the behind-the-ear unit of the hearing aid.

The plurality of electrode channel circuits may be arranged in in-the-ear unit and/or behind-the-ear unit.

The communication link may be a communication bus or a wireless communication link.

The hearing aid may comprise a housing that includes the plurality of electrode units and the plurality of electrode channel circuits. The housing may be an in-the-ear hearing aid.

The first DC offset voltage unit may be denoted a DC servo loop.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIGS. 6A and 6B: illustrate an example of an electrode channel circuit;

DETAILED DESCRIPTION

Figures 1A, 1B:
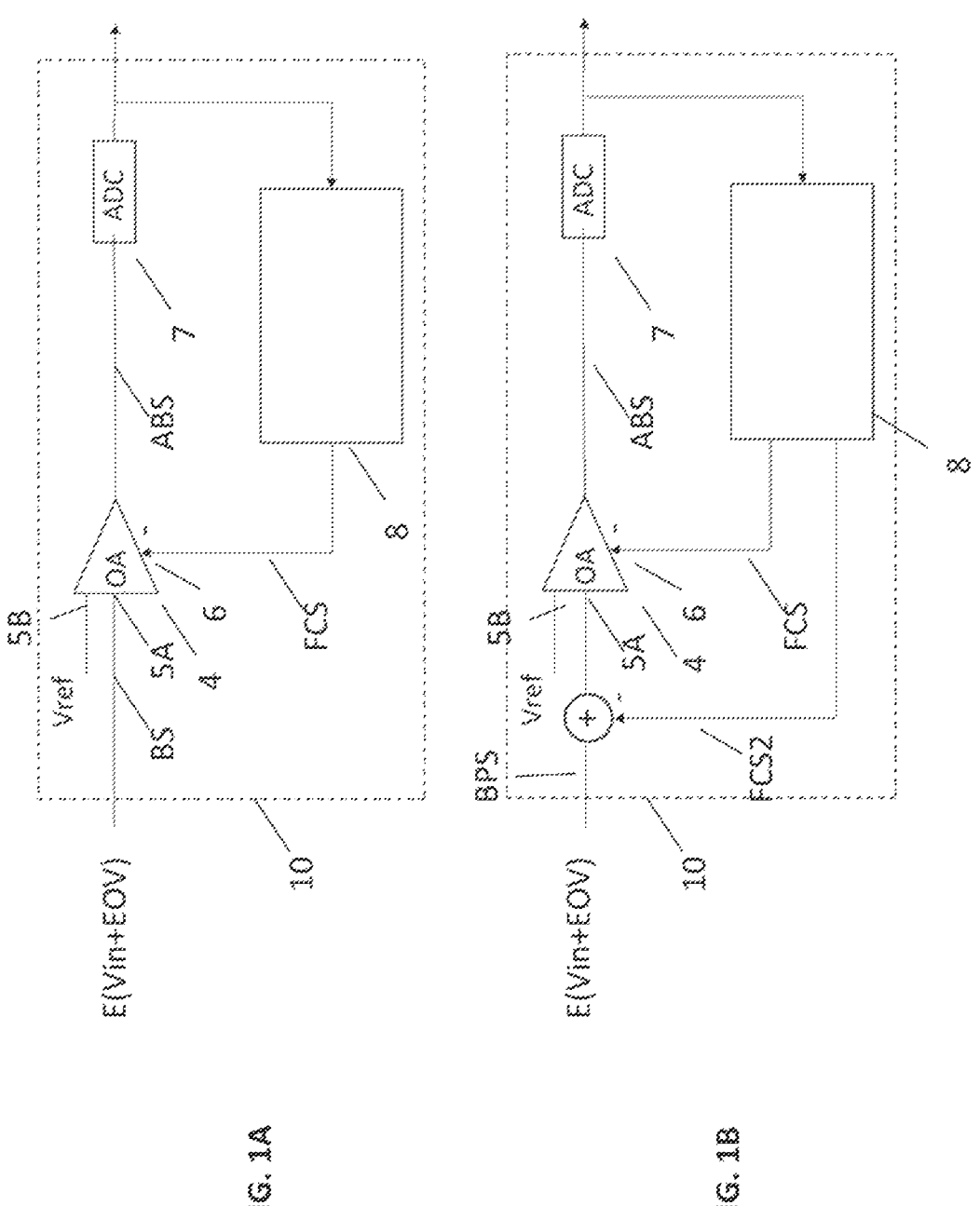
FIGS. 1A and 1B: illustrate an example of an electrode channel circuit.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the hearing aid is described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing aid is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss. The "hearing instrument" may further refer to a device such as a hearable, an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user. The hearing instrument is adapted to be worn in any known way. This may include i) arranging a unit of the hearing instrument behind the ear with a tube leading air-borne acoustic signals into the ear canal or with a receiver/loudspeaker arranged close to or in the ear canal and connected by conductive wires (or wirelessly) to the unit behind the ear, such as in a Behind-the-Ear type hearing aid, and/or ii) arranging the hearing instrument entirely or partly in the pinna and/or in the ear canal of the user such as in an In-the-Ear type hearing aid or In-the-Canal/Completely-in-Canal type hearing aid, or iii) arranging a unit of the hearing instrument attached to a fixture implanted into the skull bone such as in a Bone Anchored Hearing Aid or a Cochlear Implant, or iv) arranging a unit of the hearing instrument as an entirely or partly implanted unit such as in a Bone Anchored Hearing Aid or a Cochlear Implant. The hearing instrument may be implemented in one single unit (housing) or in a number of units individually connected to each other.

A hearing aid 1 comprises a plurality of electrode units, where each of the plurality of electrode units includes an electrode configured to provide an electrical stimulation to a user of the hearing aid and/or to measure a bio response signal (BS) of the user. The hearing aid comprises a plurality of electrode channel circuits, where each of the plurality if electrode channel circuits is connected to one or more of the electrode units. Now referring to FIGS. 1A and 1B, an electrode channel circuit 10 of the plurality of electrode channel circuits is illustrated. The electrode channel circuit 10 includes an operational amplifier 4 comprising a first input terminal 5A configured to receive the bio response signal (BS) and provide an amplified bio response signal (ABS). The operational amplifier 4 may be a differential operational amplifier, where the first input terminal is a differential input terminal where the bio response signal (BS) represent differential signals. The electrode channel circuit 10 may be connected to at least two of the plurality of electrode units. For example, the electrode channel circuit 10 may be connected to a first electrode unit and a second electrode unit, where the second electrode unit is a common electrode unit for at least two electrode channel circuits of the plurality of electrode channel circuits. The bio response signal of the user may be a combination of an input of the two electrode units. In FIG. 1A, the electrode channel circuit 10 includes a first DC offset unit 8 configured to reduce the impact of DC offset in the electrode channel circuit 10 by receiving a digital part 7 of the amplified bio response signal (ABS) and converting it to a feedback current signal (FCS) which is transmitted to a first load input 6 of the operational amplifier 4 for providing balanced drain currents in the operational amplifier 4. In FIG. 1B, the first DC offset unit 8 is configured to provide another feedback current signal (FCS2) which is then transmitted to the first input terminal 5A of the operational amplifier combined 4 with the bio response signal (BS).

In the remaining illustrations of the electrode channel circuit 10, the circuit 10 includes a Programmable Gain Amplifier (PGA) for providing a programmable gain to the amplified bio response signal. The PGA is optionally.

Figure 2:
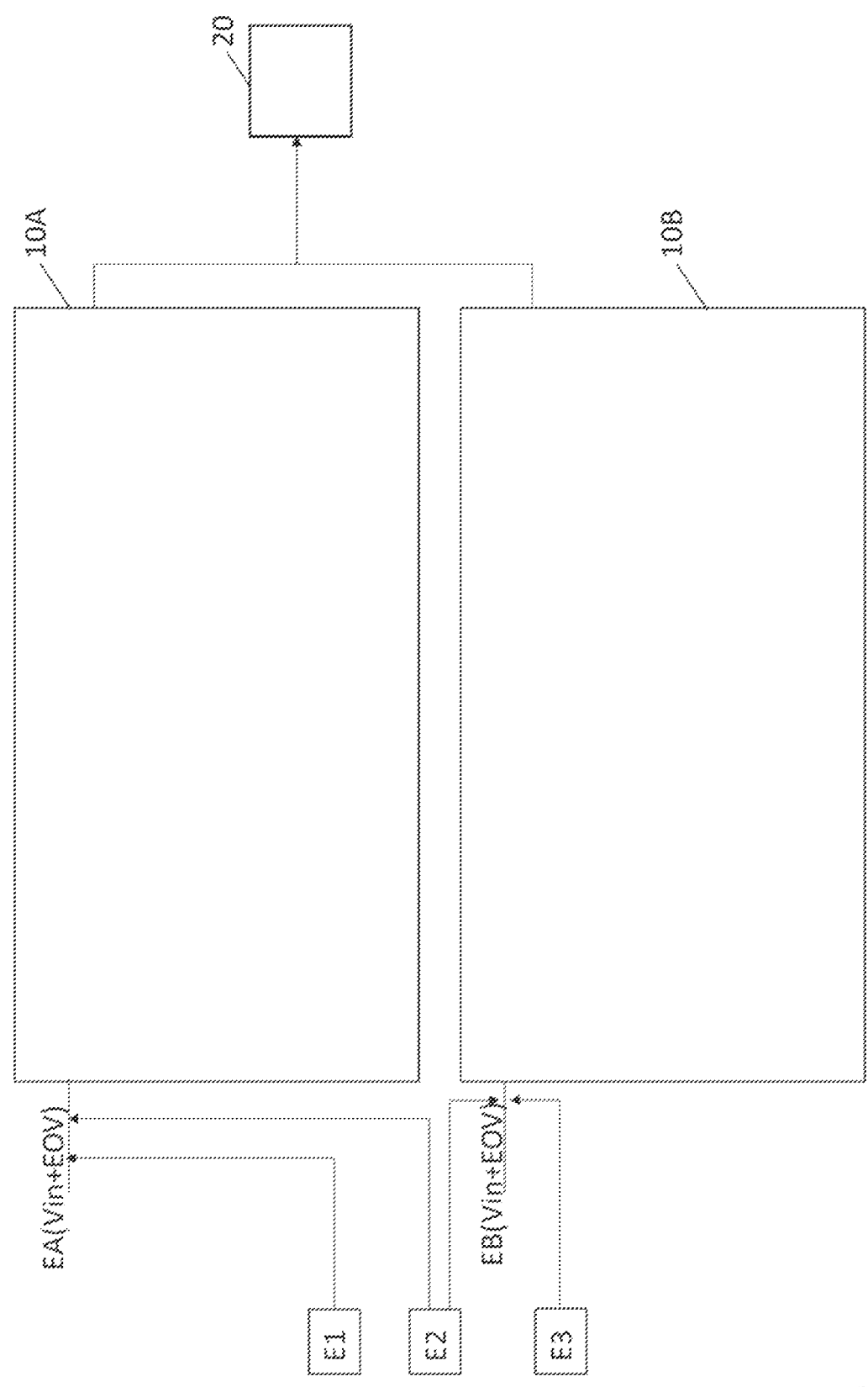
FIG. 2 illustrates an example of a plurality of electrode channel circuits.

FIG. 2 illustrates an example of the plurality of electrode channel circuits including a first electrode channel circuit 10A and a second electrode channel circuit 10B that are combined either via a digital control unit 20 or a digital filter 20. In this present example, the output of the two channels (10A, 10B) are combined via a digital control unit 20. The first electrode channel circuit 10A is connected to a first electrode unit and a second electrode unit of the plurality of electrode units, and the second electrode channel circuit 10B is connected to the second electrode unit and a third electrode unit, wherein the second electrode unit is acting as a common electrode unit for both electrode channel circuits (10A, 10B). The first electrode channel circuit 10A receives a bio response signal BS from both the first electrode E1 and the common electrode E2 and which provides an electrode voltage input (EA(Vin)) and an offset electrode voltage (EA(EOV)) to the first electrode channel circuit 10A. Similar, the second electrode channel circuit 10B receives a bio response signal BS from both the third electrode E3 and the common electrode E2 and which provides an electrode voltage input (EB(Vin)) and an offset electrode voltage (EB(EOV)) to the second electrode channel circuit 10B.

Figure 3A:
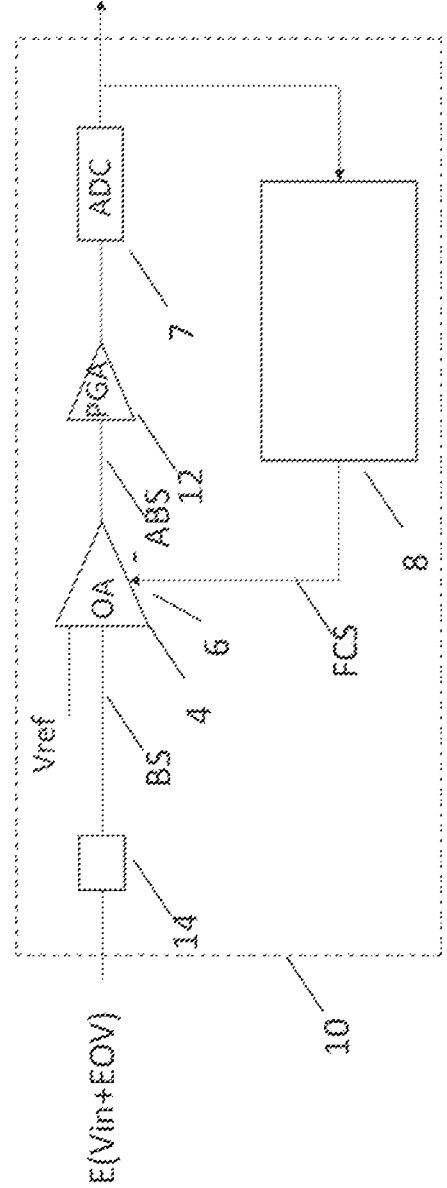
FIGS. 3A and 3B: illustrate another example of the electrode channel circuit.
Figure 3B:
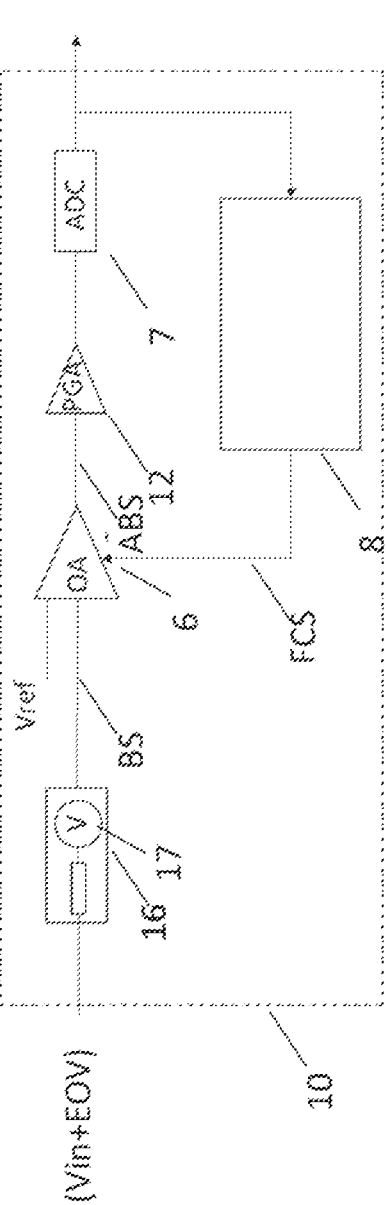

FIGS. 3A and 3B illustrate further examples of the electrode channel circuits 10. In these present examples the first DC offset unit 8 is similar to the one depicted in FIG. 1A, however, the first DC offset unit 8 illustrated in FIG. 1B may be used instead. In FIG. 3A the electrode channel circuits 10 includes a second DC offset unit 14 configured to receive the bio response signal (BS) and reduce the DC offset in the electrode channel circuit. The bio response signal with reduced DC offset is forwarded to the operational amplifier 4. In FIG. 3B, the electrode channel circuits 10 includes an impedance matching unit 16 configured to receive the bio response signal (BS) and to match a first impedance of a first electrode unit (E1) of the plurality of electrode units (E) to at least a second impedance of a second electrode unit (E2) of the plurality of electrode units (E). In this present example, the impedance matching unit 16 is configured to measure 17 an output voltage of the impedance matching unit 16, and based on the output voltage the impedance matching unit 16 is configured to adapt the impedance of the first electrode E1.

Figure 4:
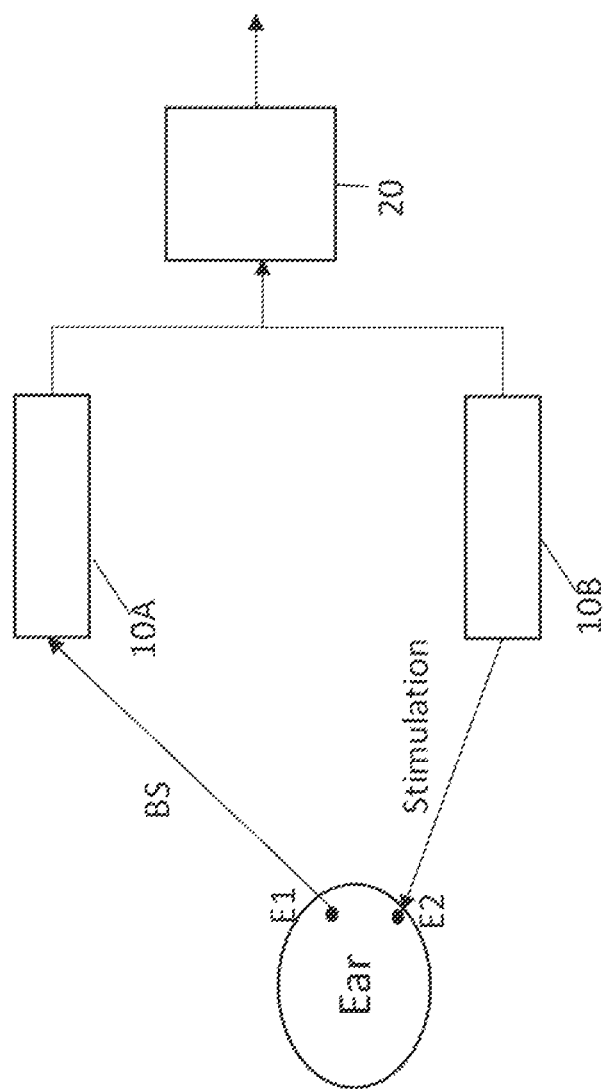
FIG. 4: illustrates an example of determining electrode impedance.

The hearing aid 1 includes a stimulator unit configured to transmit an alternating current, a direct current or a combination of the alternating current to at least an electrode unit (E) of the plurality of electrode units via the electrode channel circuit 10 of the plurality of electrode channel circuits, and where the at least electrode unit (E) is configured to apply the electrical stimulation based on the current to the user. In one example, the stimulator unit may be configured to distribute the current to each of the plurality of electrode channel circuits, and that each of the plurality of electrode channel circuits 10 is configured to forward the current to one or more electrode units (E). In another example, a stimulator unit may be arranged in each of the plurality of electrode channel circuits 10. FIG. 4 illustrates an example where a second electrode unit E2 is configured to apply a stimulation based on an alternating current, a direct current or a combination of an alternating current provided by the stimulator unit via a second electrode channel circuit 10B. The current may be transmitted to the second electrode unit E2 from the stimulator unit and through the impedance matching unit 16A of the second electrode channel circuit 10B. A first electrode unit E1 receives a bio response signal (BS) and forwards the signal (BS) to a first electrode channel circuit 10A. The bio response signal (BS) passes through an impedance matching unit 16 of the first electrode channel circuit 10A. The impedance matching unit 16 of the first electrode channel circuit 10A is configured to measure output voltages of the unit 16, and based on the output voltages a resistive impedance and/or a reactive impedance are determinable.

Figure 5A:
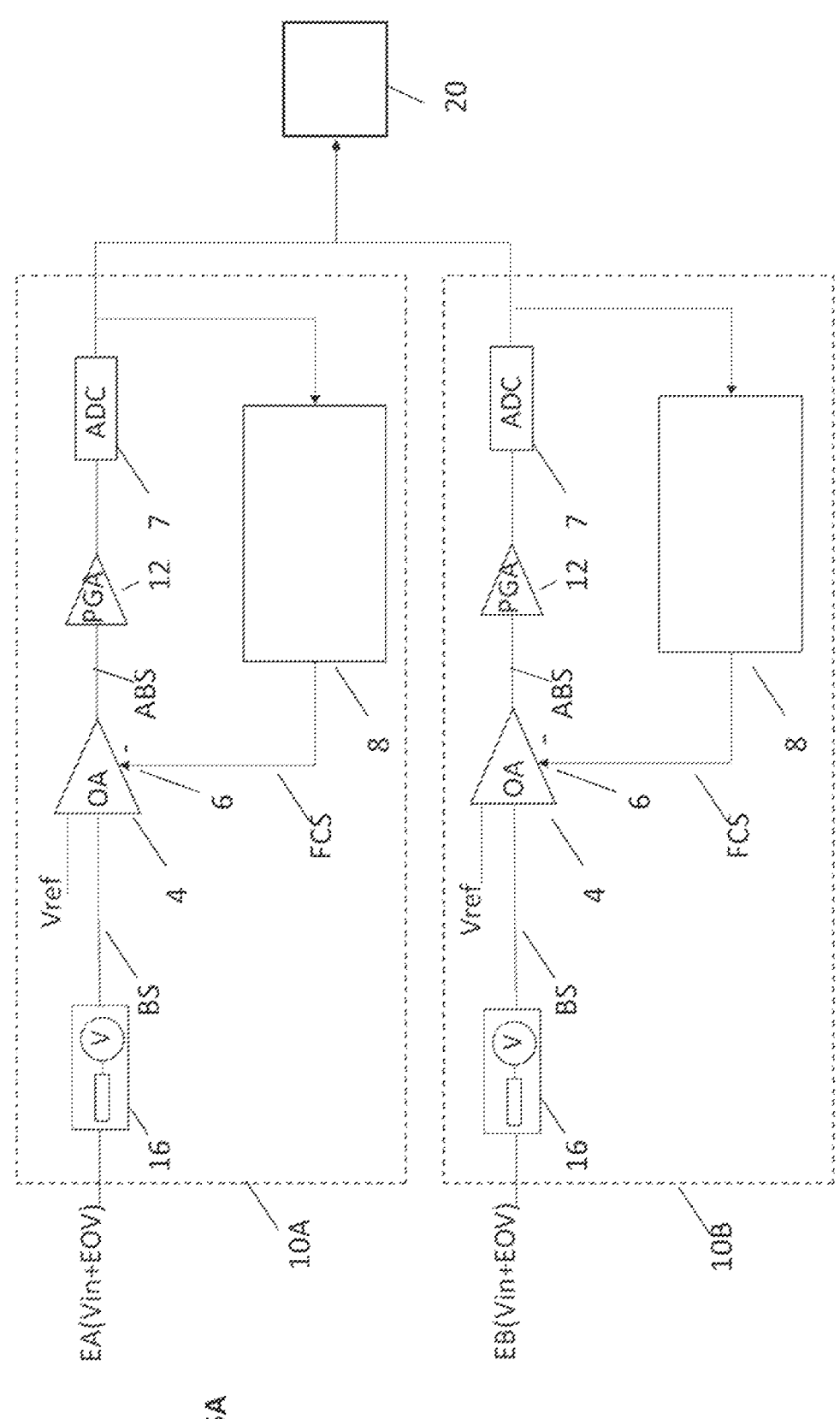
FIGS. 5A and 5B: illustrate examples of a plurality of electrode channel circuits.
Figure 5B:
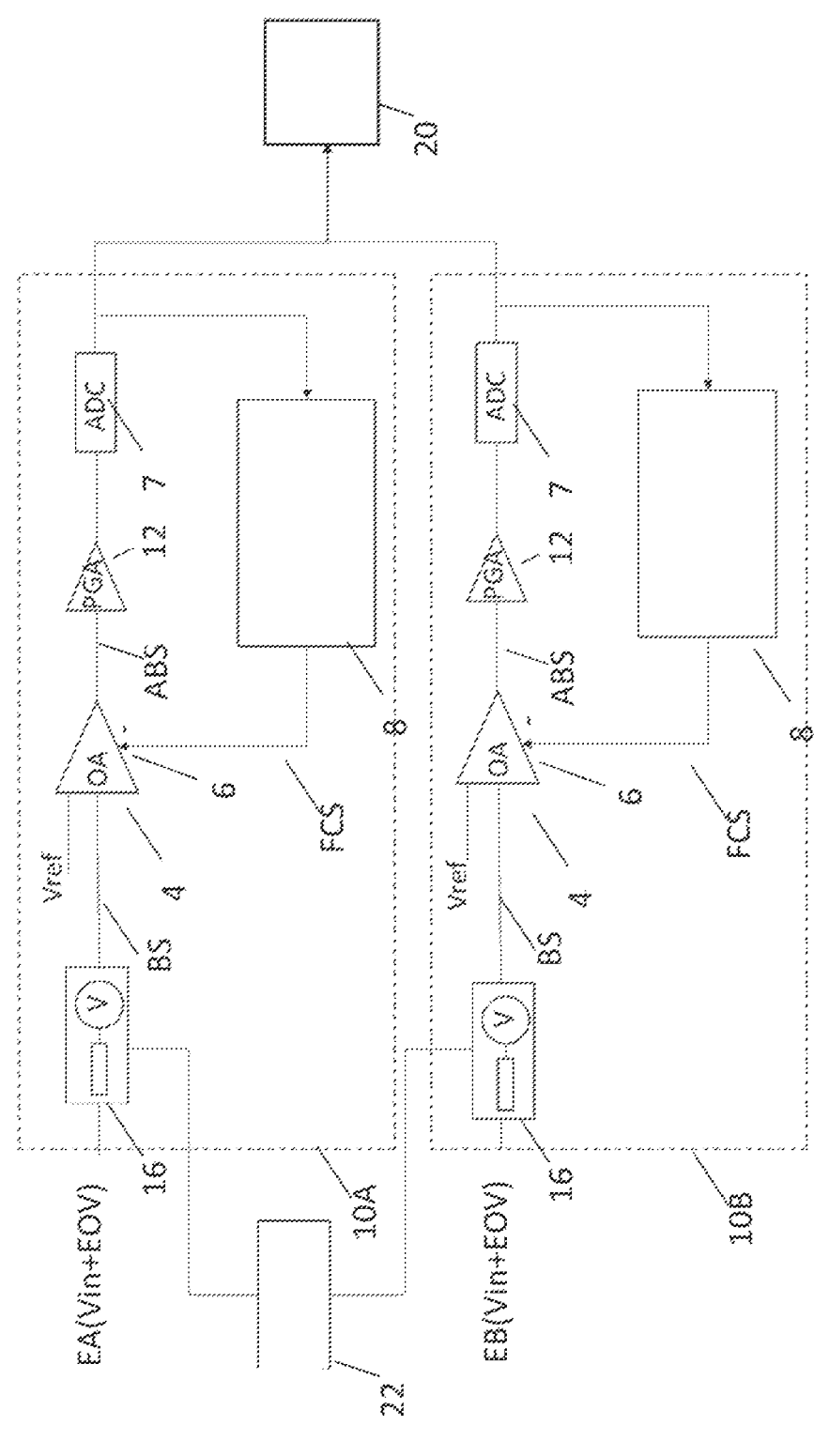

FIGS. 5A and 5B illustrate an example of two electronic channel circuits (10A, 10B) connected via a digital control unit 20. In this present example, both circuits (10A, 10B) include an impedance matching unit 16, which in FIG. 5A illustrates an example where the determining of the impedances of a respective impedance matching unit 16 is done in the respective impedance matching unit 16, and in FIG. 5B, the impedances of a respective impedance matching unit 16 is determined via an impedance processor unit 22.

In other examples the DAC 7 of both channels (10A, 10B) could be removed and replaced with a single DAC arranged at the output of the combiner unit 20.

The impedance processor unit 22 may be connected to each of the impedance matching unit 16 of the plurality of electrode channel circuits (10A, 10B).

FIGS. 6A and 6B illustrate an example of the electrode channel circuits 10 including at least the impedance matching unit 16 and the second DC offset unit 14. The electrode channel circuit 10 receives the bio response signal (BS) via the impedance matching unit 16 and forward the impedance matched bio response signal (BS) to the second DC offset unit 14. The second DC offset unit 14 reduces the DC offset voltage that may appear in the bio response signal (BS) and transmits the bio response signal with reduced DC offset voltage to the operational amplifier 4. The first DC offset unit 8 receives a part of the amplified bio response signal from the operational amplifier 4 and provides a feedback current signal to the operational amplifier 4 for the purpose of balancing the drain currents in the operational amplifier. The balanced drain current results in a further reduced DC offset voltage in the amplified bio response signal (ABS). In both figures, the first DC offset voltage 8 is different.

Figures 7A, 7B:
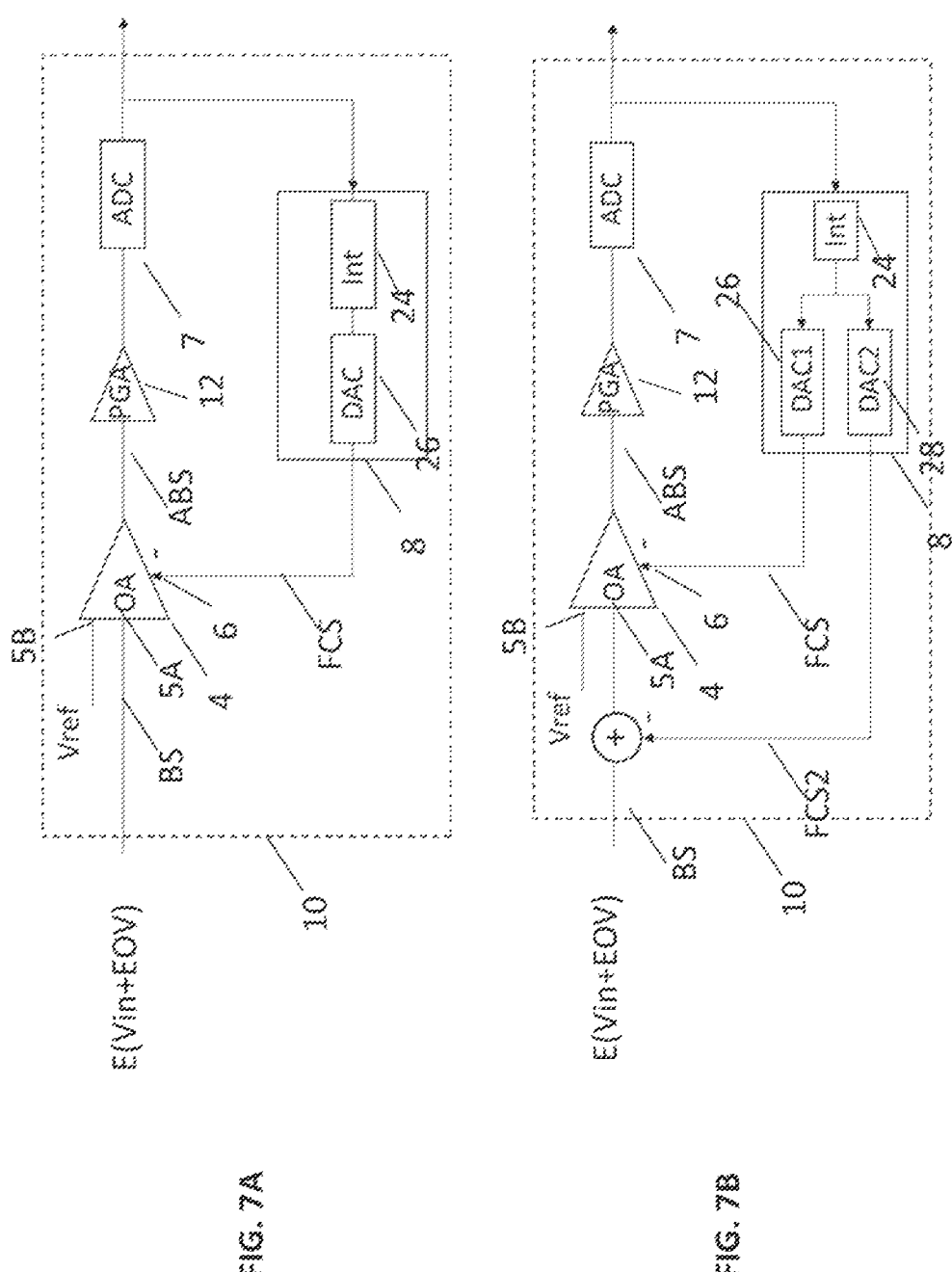
FIGS. 7A through 7D: illustrate an example of an electrode channel circuit.

FIGS. 7A to 7E illustrate different examples of the first DC offset voltage unit 8 in one configuration of the electrode channel circuit 10. Similar examples of the first DC offset voltage unit 8 may appear in different configurations of the electrode channel circuit 10. In FIG. 7A, the first DC offset voltage unit 8 includes an offset correction circuit 24 configured to receive the amplified bio response signal (ABS) that is converted to a digital electrical signal via the analog-to-digital converter 7. The offset correction circuit 24 is configured to integrate the digital electrical signal and provide a digital offset correction signal that is equal to the undesired DC offset voltage in the amplified bio response signal (ABS) based on the integration of the digital electrical signal. The digital offset correction signal is then converted to the feedback current signal (FCS) via a first digital-to-analog converter 26 and transmitted to the first load input 6 of the operational amplifier 4.

FIG. 7B illustrates another example of the first DC offset voltage unit 8. In this present example the first DC offset voltage unit 8 is similar to the one described in FIG. 7A, although, now the first DC offset voltage unit 8 includes a second digital-to-analog converter 28 configured to receive the digital offset correction signal and convert it to another feedback current signal FCS2 which is then transmitted to the first input terminal of the operational amplifier combined with the bio response signal. The second digital-to-analog receives the digital offset correction signal from the offset correction circuit 24 and provides the another feedback current signal FCS2 to the first input. Thereby, the DC offset voltage in the bio response signal is compensated before the operational amplifier 4 and within the operational amplifier 4 resulting in a more reliable amplified bio response signal in view of known art.

Figure 7C:
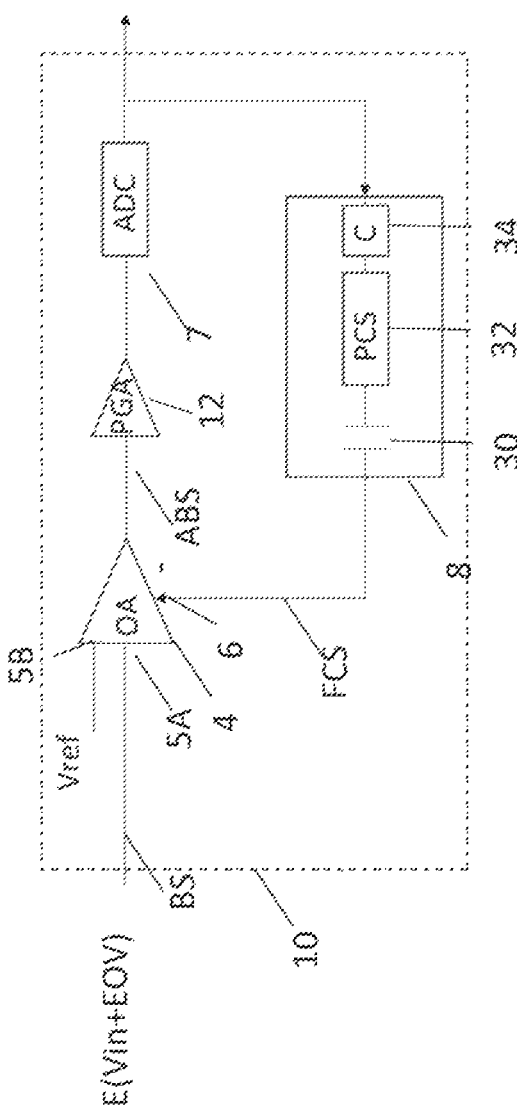

FIG. 7C illustrates yet another example of the first DC offset unit 8. In this present example, the unit 8 includes a controller 34 configured to provide a control signal based on the digital electrical signal provided by the ADC 7. The unit 8 includes an offset storage capacitor 30 connected to the first load input 6, or alternatively, to the first input terminal 5A of the operational amplifier 4. The unit 8 includes a pulse current source 32 configured to increase or decrease in discrete steps a voltage level of the offset storage capacitor 30 based on the control signal. The offset storage capacitor 30 is configured to maintain the voltage level at a level proportional to a DC offset voltage at the first input terminal 5A or at the first load input 6 for providing the balanced drain currents of the operational amplifier 4. The controller 34 is configured to determine the discrete steps by changing a magnitude and/or a duration of the current pulses provided by the pulse current source 32.

Figure 7D:
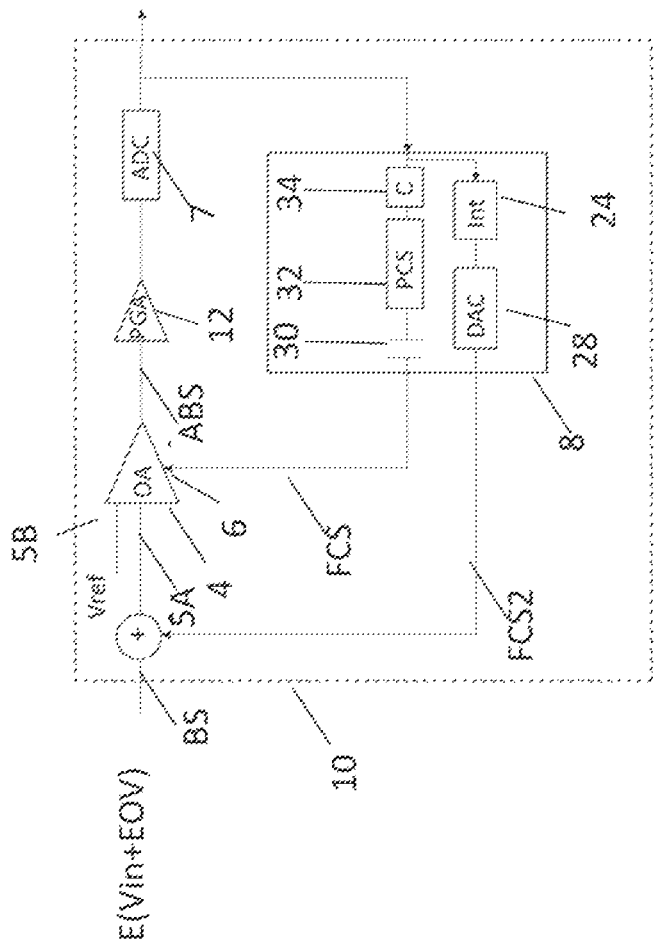

FIG. 7D illustrates another example of the first DC offset unit 8 similar to the first DC offset unit 8 illustrated in FIG. 7B, where the first digital-to-analog converter 26 is replaced by the controller 34, the offset storage capacitor 32 and the pulse current source 32.

Figures 8A, 8B:
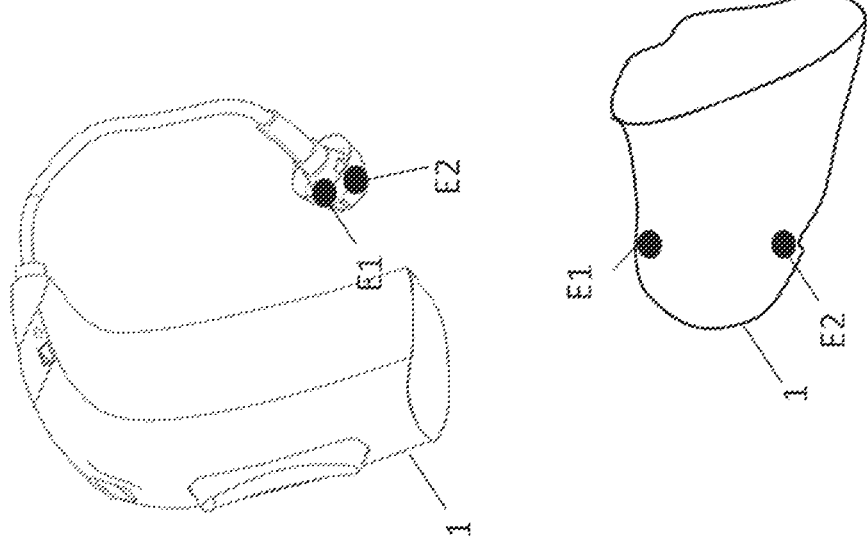
FIGS. 8A and 8B: illustrate an example of a hearing aid.

FIGS. 8A and 8B illustrate different examples of the hearing aid 1 including the plurality of electrodes channel circuits. In FIG. 8A the at least two of the plurality of electrode units (E1, E2) are arranged on an earpiece connected to a behind-The-Ear (BTE) hearing aid. The connection between the BTE and the earpiece is provide by an I3C wire. In one communication mode the I3C wire is configured to communicate between the plurality of electrode units and the plurality of electrode channel circuits which may be arranged in the BTE. In a second communication mode the I3C wire communicates power and/or data not relating to communication of bio response signals. In FIG. 8B, the hearing aid 1 is In-The-Ear hearing aid where the electrodes are arranged on the housing of the hearing aid 1.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more". Unless specifically stated otherwise, the term "some" refers to one or more.

The invention claimed is:

1. A hearing aid comprising;
a plurality of electrodes, where each of the plurality of electrodes is configured to provide an electrical stimulation to a user of the hearing aid and/or to measure a bio response signal of the user;
a plurality of electrode channel circuits, where each of the plurality of electrode channel circuits includes:
an operational amplifier comprising a first input terminal configured to receive the bio response signal and provide an amplified bio response signal, and the operational amplifier includes a first load input;
a first DC offset unit configured to reduce the impact of DC offset in the electrode channel circuit of the plurality of electrode channel circuits by receiving a part of the amplified bio response signal and converting the received part of the amplified bio response signal to a feedback current signal which is transmitted to the first load input for providing balanced drain currents in the operational amplifier;
an analog-to digital converter wherein the amplified electrical response signal is converted to a digital electrical signal via the analog-to-digital converter;
wherein the first DC offset unit includes:
a controller configured to provide a control signal based on the digital-electrical signal, an offset storage capacitor connected to the first input terminal of the operational amplifier or the first load input,
a pulse current source configured to increase or decrease in discrete steps a voltage level of the offset storage capacitor based on the control signal, and
wherein the offset storage capacitor is configured to maintain the voltage level at a level proportional to a DC offset voltage at the first input terminal or at the first load input for providing the balanced drain currents of the operational amplifier.

2. A hearing aid according to claim 1,
wherein each of the plurality of electrode channel circuits includes a second DC offset unit configured to receive the bio response signal and reduce the impact of DC offset and forward the bio response signal, and
wherein the second DC offset unit includes a shunt impedance circuit including multiple shunt resistors and a voltmeter configured to measure an output voltage of an output of the second DC offset unit.

3. A hearing aid according to claim 1, wherein each of the plurality of electrode channel circuits includes an impedance matching circuit configured to receive the bio response signal and to match a first impedance of a first electrode of the plurality of electrodes to at least a second impedance of a second electrode of the plurality of electrodes.

4. A hearing aid according to claim 3, wherein the impedance matching circuit is configured to receive the bio response signal and forward the impedance matched bio response signal to the operational amplifier or to the second DC offset unit.

5. A hearing aid according to claim 3, wherein an alternating current, a direct current or a combination of an alternating current and a direct current is applied to an electrode of the plurality of electrodes via the impedance matching circuit of an electrode channel circuit of the plurality of electrode channel circuits, and where the electrode is configured to apply the electrical stimulation based on the current.

6. A hearing aid according to claim 5, wherein a second impedance matching circuit of a second electrode channel circuit of the plurality of electrode channel circuits is configured to measure a plurality of impedances of a second electrode of the plurality of electrodes, and based on the plurality of measured impedances both a resistive impedance and a capacitive impedance of the second electrode of the plurality of electrodes are determined in the second impedance matching circuit or in an impedance processor unit of the hearing aid.

7. A hearing aid according to claim 1, comprising an analog-to-digital converter, wherein the amplified bio response signal is converted to a digital electrical signal via an analog-to-digital converter, and the first DC offset unit further includes:
an offset correction circuit configured to receive the digital electrical signal and provide a digital offset correction signal based on a measure of a DC offset voltage in the digital electrical signal,
a digital-to-analog converter configured to receive the digital offset correction signal and convert it to the feedback current signal which is then transmitted to the first load input of the operational amplifier.

8. A hearing aid according to claim 1, wherein the controller is configured to determine the discrete steps by changing a magnitude and/or a duration of the current pulses provided by the pulse current source.

9. A hearing aid according to claim 1, wherein the pulsed current source is turned on and off based on an input from the controller, where a DC offset is detected or a DC offset that is above a DC offset threshold is detected by the controller, the pulsed current source is turned on, and where a DC offset is not detected or a DC offset that is below a DC offset threshold is detected by the controller, the pulsed current source is turned off.

10. A hearing aid according to claim 2, wherein the impedance matching circuit is configured to match the first impedance to the at least second impedance based on a first measured output voltage of a primary second DC offset unit connected to the first electrode and on a second measured output voltage of a secondary second DC offset unit connected to the second electrode.

11. A hearing aid according to claim 1, wherein the hearing aid is configured to compensate a hearing loss of a user of the hearing aid, comprising;
a microphone configured to receive an acoustic wave and provide an audio signal based on the acoustic wave,
a signal processor unit configured to process the audio signal and provide a processed audio signal;
an output transducer configured to output the processed audio signal to the user,
and wherein the signal processor unit is configured to process the audio signal based on the amplified bio response signal or is configured to adapt a hearing profile stored within a memory of the hearing aid based on the amplified bio response signal.

12. A hearing aid according to claim 1, comprising;
an in-the-ear unit;
a behind-the-ear unit;
a communication link configured to provide an electrical connection between the in-the-ear unit and the behind-the-ear unit,
a processor unit configured to receive the amplified bio response signal via the communication link, and
wherein one or more of the plurality of electrodes are arranged in the in-the-ear unit, and the processor unit is arranged in the behind-the-ear unit of the hearing aid.

13. A hearing aid according to claim 12, wherein the communication link is a communication bus or a wireless communication link.

14. A hearing aid according to claim 1, comprising a housing that includes the plurality of electrodes and the plurality of electrode channel circuits.

15. A hearing aid according to claim 2, wherein each of the plurality of electrode channel circuits includes an impedance matching unit circuit configured to receive the bio response signal and to match a first impedance of a first electrode of the plurality of electrodes to at least a second impedance of a second electrode of the plurality of electrodes.

16. A hearing aid according to claim 3, wherein the impedance matching circuit is configured to receive the bio response signal and forward the impedance matched bio response signal to the operational amplifier or to the second DC offset unit.

17. A hearing aid comprising;
a plurality of electrode units, where each of the plurality of electrode units includes an electrode configured to provide an electrical stimulation to a user of the hearing aid and/or to measure a bio response signal of the user;
a plurality of electrode channel circuits, where each of the plurality of electrode channel circuits is connected to a re includes:
a DC offset unit configured to receive the bio response signal and reduce the impact of DC offset in the bio response signal and forward the bio response signal;
an operational amplifier comprising a first input terminal configured to receive the bio response signal forwarded by the and provide an amplified bio response signal, and the operational amplifier includes a first load input;
wherein each of the plurality of electrode channel circuits includes an impedance matching circuit configured to receive the bio response signal and to match a first impedance of a first electrode unit of the plurality of electrode units to at least a second impedance of a second electrode unit of the plurality of electrode units; and
wherein the DC offset unit of each electrode channel circuit includes a shunt impedance circuit including multiple shunt resistors and a voltmeter configured to measure an output voltage of an output of the DC offset unit, and
wherein the impedance matching circuit of each of the plurality of electrode channel circuits is configured to match the first impedance to the at least second impedance based on a first measured output voltage of the voltmeter of the DC offset unit of the corresponding electrode channel circuit and on a second measured output voltage of the voltmeter of the DC offset unit of another of the plurality of electrode channel circuits.

18. A hearing aid according to claim 17, further comprising:
another DC offset unit configured to reduce the impact of DC offset in the electrode channel circuit of the plurality of electrode channel circuits by receiving a part of the amplified bio response signal and converting the received part of the amplified bio response signal to a feedback current signal which is transmitted to the first load input for providing balanced drain currents in the operational amplifier; and
an analog-to-digital converter, wherein the amplified bio response signal is converted to a digital electrical signal via an analog-to-digital converter,
wherein the another DC offset unit includes:
an offset correction circuit configured to receive the digital electrical signal and provide a digital offset correction signal based on a measure of a DC offset voltage in the digital electrical signal,
a first digital-to-analog converter configured to receive the digital offset correction signal and convert it to the feedback current signal which is then transmitted to the first load input of the operational amplifier.

\* \* \* \* \*